United States Patent [19]
Phelan

[11] Patent Number: 6,045,516
[45] Date of Patent: Apr. 4, 2000

[54] CLEANABLE MEDICAL/SURGICAL SUCTION DEVICES

[76] Inventor: James Phelan, 204 Shadow Lake Dr., Lilburn, Ga. 30047

[21] Appl. No.: 09/215,238

[22] Filed: Dec. 18, 1998

[51] Int. Cl.[7] ....................................................... A61B 5/00
[52] U.S. Cl. .............................. 600/579; 604/119; 433/91
[58] Field of Search ..................................... 604/118, 119, 604/902, 905; 433/91, 94, 95; 600/573, 578, 579, 580, 581

[56] References Cited

U.S. PATENT DOCUMENTS

| | | |
|---|---|---|
| D. 233,264 | 10/1974 | Geraci et al. . |
| D. 241,476 | 9/1976 | Lahay . |
| D. 247,915 | 5/1978 | Lahay . |
| D. 364,456 | 11/1995 | Solnit et al. . |
| 2,531,730 | 11/1950 | Henderson . |
| 2,711,586 | 6/1955 | Groves . |
| 3,516,160 | 6/1970 | Leffler . |
| 3,807,048 | 4/1974 | Malmin . |
| 3,863,635 | 2/1975 | Swatman . |
| 3,963,028 | 6/1976 | Cooley et al. . |
| 4,083,115 | 4/1978 | McKelvey . |
| 4,805,611 | 2/1989 | Hodgkins ........................... 128/207.14 |
| 4,878,900 | 11/1989 | Sundt . |
| 5,013,300 | 5/1991 | Williams ................................. 604/119 |
| 5,520,651 | 5/1996 | Sutcu et al. . |
| 5,723,840 | 3/1998 | Bojic et al. . |

*Primary Examiner*—Cary O'Connor
*Assistant Examiner*—Pamela Wingood
*Attorney, Agent, or Firm*—Eric P. Schellin

[57] ABSTRACT

A medical/surgical suction device of three essential main parts. The first part is a metal tube having a proximal port and a distal port. The proximal part is attached to a have or flexible tube that is connected to a vacuum source. The distal end has plugged into it a portion of a sleeve. The other portion of the sleeve extends therefrom and carries coaxially the a thin tube. The other end is the suction end. The sleeve may be de-mounted from the metal tube whereby the sleeve may be cleaned apart from the metal tube. The metal tube has a port intermediate its proximal part and its distal part which acts as a valve to permit.

3 Claims, 1 Drawing Sheet

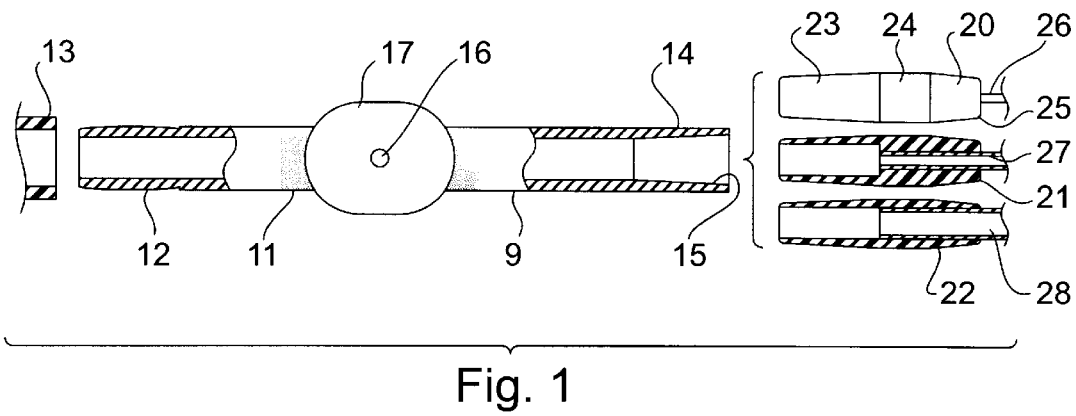
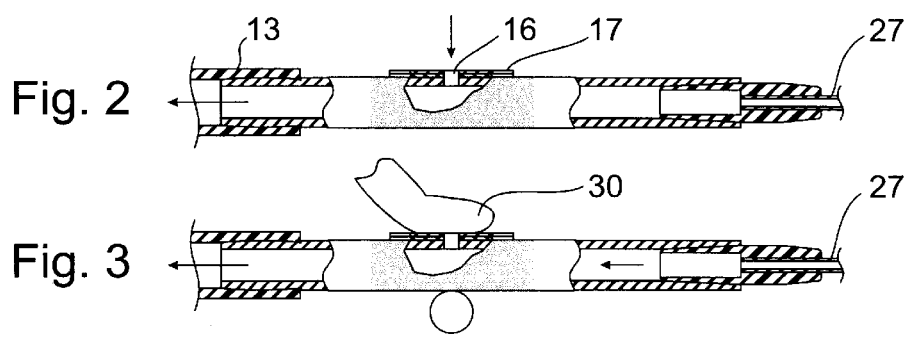
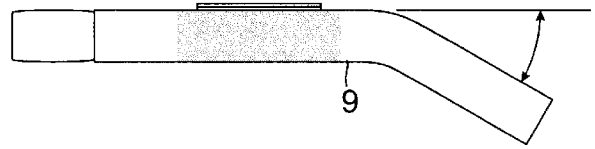
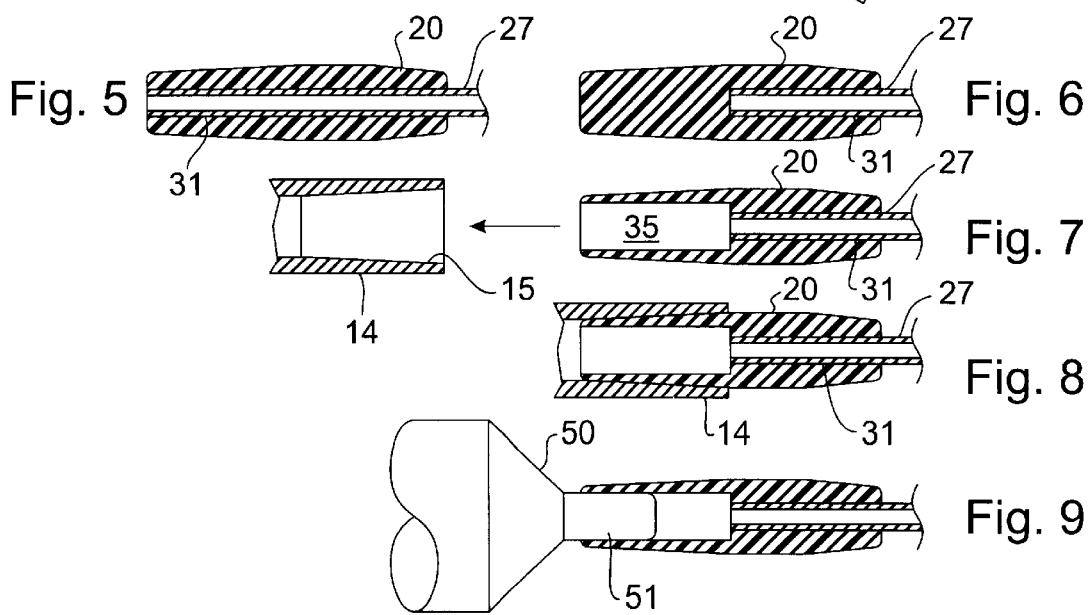

CLEANABLE MEDICAL/SURGICAL SUCTION DEVICES

The present invention relates to suction devices of the type disclosed in my co-pending application Ser. No. 09/072,494, filed May 5, 1998. This application is incorporated herein by reference in its entirety.

BACKGROUND OF THE INVENTION

Field of the Invention

The need for surgical suction devices has been well documented and demonstrated in the prior art. In general, and its simplest form, these devices constitute elongated tubes of small but varying diameters; usually, they are less than a foot in length. The proximal end is fitted to a flexible rubber or plastic tube which in turn is fitted to a vacuum source. The distal end of the elongated tube is inserted into an open wound of a patient. Fluid pooling in the environs of the wound is sucked by the elongated tube at that distal end; through the suction tube and through the flexible rubber tube for final disposal.

These suction tubes are difficult to clean as they are generally of small bore. When employing plastic as the construction material they are considered to be disposable.

The suction tube is oftentimes supplied with a side port that is close to its proximal end. At rest the suction draws air through the side port and therefor no suction is at the suction device's distal end. The user of the device, when it is desirous to effect a suction gradient at the said distal end, closes the side port by applying a thumb or finger over the side port. The side port together with the thumb of the users act as a valve for the suction device. It will be seen that the device can be easily held by one hand with the thumb of the hand being strategically positioned close to the side port for positioning thereon as needed.

As was stated, such suction devices of the prior art, are frequently made of plastic. While, because of the cheapness of plastic such suction device may be disposable, the weight of such a plastic suction device is so light that the user can hardly sense its presence in the hand so finds difficulty in effecting good control of the suction device when positioning its distal end into the site requiring aspiration.

To avoid such a light weight structure, the suction device may be made of metal, to increase the sense of presence of the device in the user's hand. However, when constructed of metal which is a more expensive material, it is advantage to use the suction device over and over again. Re-use of the suction require the need to be able to thoroughly clean the inside bore of the suction device and to be able to autoclave the suction device or to sterilize the suction device by other means.

In some prior art suction devices, the tubes are bent intermediate the ends to give enhance holding and directing of the suction device. A bend in the suction device makes it even more difficult to accomplish thorough cleaning. internally. The present suction devices are primarily designed towards general or specific "applications."

SUMMARY OF THE INVENTION

The suction device of the present invention is constructed of essentially three sections or parts. The main part consists of a stainless steel tube having a proximal end and a distal end. A rubber flexible conduit is attached to the proximal end by inserting the proximal end for a short distance into the said conduit. The stainless steel tube defines a handle portion equal to or greater in diameter of the conduct coming from the suction source.

The stainless steel tube has a port intermediate the proximal and distal end. The port has a flat platen about the port. The port together with the thumb of the user acts as a valve to the interior of the stainless tube. In other words the flat portion of the thumb of the user of the suction is employed to close the port by placing the thumb there upon and vice versa.

The distal end portion of the stainless tube is slightly internally bevelled whereby the largest diameter of the bore is at the edge portion of the distal end. The beveled portion is detailed to accept for insertion a round short DELRIN sleeve,. The latter is sloped to mate with the bevelled portion of the distal end of the stainless steel tube. The sleeve enters the said stainless steel tube for only a portion. the remaining portion of the sleeve extends for a distance beyond the stainless steel tube.

The sleeve has mounted therein a distal end portion of an elongated thin tube and is concentric with the sleeve. The thin tube extends into the sleeve about half way. The bore in the sleeve, through which the thin tube does not extend and which is in the part of the sleeve that is mounted in the distal end of the stainless steel tube, is of a bore dimension into which a luer of a syringe may be fitted when said sleeve and said thin tube is removed from its position of insertion.

It is an object of this invention, unlike current art, to provide a suction device capable of being cleaned, processed, and sterilized thereby eliminating any possibilities of cross contamination not uncommon to surgical cannulated devices. Through its design, it is the primary objective of this invention that cleaning through sterilization become universally feasible and achieved. "Applications" of current suction devices while significant and addressed by this device become secondary. This purpose and the distinguishing characteristics of it will become apparent in this application.

BRIEF DESCRIPTION OF THE DRAWINGS

FIG. 1 is an exploded top plan fragmentary view and partial fragmentary view of the suction device of the present invention;

FIG. 2 is a partial fragmentary side view;

FIG. 3 is a similar partial fragmentary side view with the finger valving being demonstrated;

FIG. 4 is a side view of the stainless steel tube having a small angle bend;

FIG. 5 is a cross sectional view of the sleeve with a fragmentary portion of the thin tube entirely therethrough;

FIG. 6 is a cross-section view of the plug which upon drilling becomes the sleeve of the present invention with the thin tube shown fragmentary;

FIG. 7 is a cross-sectional view of the sleeve of FIG. 6 shown after further machining;

FIG. 8 is a cross-sectional view of the distal end of the stainless steel tube and the sleeve mounted in place and the thin tube extending therefrom;

FIG. 9 is a cross-sectional view of the sleeve with the luer of a syringe mounted onto the sleeve.

DETAILED DESCRIPTION OF THE INVENTION

FIG. 1 depicts a stainless steel tube 11 which is part of the suction device that is hand held. It is fitted at its proximal end 12 with the end of a rubber hose or tube 13. The distal end 14 of the stainless steel tube 11 has a bore area with a flare 15. The stainless steel tube has an intermediate port 15 which is surrounded by a stainless steel flat piece 16 which is welded to tube 11.

The flare 15 takes the internal bore of the stainless steel tube from 0.25 inches in diameter to 0.28 inches. The flare itself is about 0.5 inches.

The distal end 14 is fitted with one of sleeves 20, 21 or 21. Sleeve 20 is shown in a side view and has a sloped area 23 at its proximal end which terminates in a cylindrical section 24 and has a further sloped portion 25 at its other end. Each of the sleeves possesses a similar external configuration. The differences in sleeve 20, 21 and 22, as depicted resides in the fact that each is fitted with different diameter thin tube 26 or 27 or 28. The sleeves are injection molded about the thin tubes 26 or 27 or 28. More about which will be described below. The thin tubes may be selected from a large array of sizes so is not limited to those shown by reference numerals 26 or 27 or 28. Most common bore diameters are from 3 to 18 French.

FIG. 2 shows the suction tube of the present invention in an assembled condition although hose 13 is in fragmentary condition as is thin tube 27. As assembled the source of vacuum at the end of hose 13 is shown to aspirate air through port 16.

When the hand held suction device has the distal end (not shown) of tube 27 inserted into a liquid containing wound locale, finger or thumb 30 is slightly compressed over port 16 and closes it to further ambient air aspiration, thereby transferring the source of suction to the distal end of thin tube 27 and therewith removes the pooled liquid up the thin tube 27 and through the stainless steel tube 9 and out hose 13.

FIG. 4 depicts a more convenient stainless steel tube which has an acute angle bend located between the distal end 14 and the port 16.

FIG. 5 shows sleeve 20, for instance, which has been injection molded with DELRIN around the proximal portion 31 of this tube 27 prior to further machining.

Then in FIG. 6, the proximal portion 31 of the thin tube 27 is only part way through sleeve 20 so that the sleeve is not yet completely formed.

FIG. 7 depicts the sleeves of FIG. 5 or FIG. 6 which has a cavity drilled axially form the proximal portion of the sleeve to produce cavity 35. The diameter of the cavity is from 0.167 inches to 0.169 inches. The depth of the cavity is about 0.5 inches In drilling the embodiment of FIG. 5 the thin tube is also drilled out with applicable portions of the DELRIN material removed to produce cavity 35. In FIG. 6, only the DELRIN is drilled out to a point where there is communication with the proximal end of thin tube 27.

FIG. 7 shows finished sleeve 20 with its thin tube 27 mounted therein, being thrust for fitment in the distal end 14 of the stainless steel tube.

FIG. 8 depicts the view of the fitted assembly of the stainless steel tube, sleeve and the thin tube 27 in functioning condition.

Finally, FIG. 9 shows the sleeve 20 and its thin tube 27 dissembled from the stainless tube. A fragmentary syringe is shown with the luer 51 thereon mounted into cavity 35 of the sleeve. Wash fluid may then be squirted through thin-tube 27 to cleanse the thin tube. The stainless steel tube 9 being of larger diameter may be cleaned by brush means or the like.

The present invention derives its special applicblity form the feel that it is comprised of three essential parts wherein the sleeve and its concomitant thin tube an be disassembled form the stainless steel tube. Each of the parts may be cleaned separately and therefor thoroughly. The arrangement avoid a single lengthy suction tube which by shear length would encounter cleaning difficulties.

The invention has the further advantage of making it possible to at least provide for the disposal of the sleeve with the thin tube should it be impossible to clean thoroughly. The sleeve and thin tube is much least expensive then the stainless tube handle portion 9.

The thin tube may be constructed of a less expensive material then stainless steel such as aluminum.

As stated in the above the use of a stainless tube 9 as a handle provides for better weight distribution and feel. The feel may be also enhanced by giving a sand blasted finish to the stainless steel tube about the port 15 giving a contrasting feel to the stainless tube 9.

It is contemplated that other plastic, other than DELRIN may be used. a controlling criteria is in the ability to be autoclavable.

The stainless steel tube handle 9 is manufactured of surgical grade stainless steel. The outer diameter is 0.35 inches. The inner diameter is 0.25 inches except for the 0.5 inch flare 15 portion which expands to 0.28 inches. Said flare portion facilitates consistent acceptance and release of the sleeve carrying the said thin tube 27, for instance. The large bore of the handle portion 9 results in the inner bore being visually observable even when the stainless tube handle 9 is angled. The preferred length of the stainless steel tube handle in about 3.5 inches.

The said large bore makes it possible to accept all bristled (fiber or steel one-quarter up to one-third inch) cleaning brushes.

The sleeves 21, 22, 23 have a length of approximately 1 inch. All are 0.25 inches in diameter at the proximal end and gradually taper distally to 0.28 inch. This taper is 0.5 inch in length. The 0.28 inch is 0.25 inch in length before tapering gradually to its distal end.

The cavity 35 is 0.167 inch to 0.169 inch in diameter. It begins at the proximal (joinder) end and is 0.5 inch in towards the sleeve's center. This cavity services as a "flush-port" to the "working" element of the suction probe in that it accommodates the luer of universally sized syringes. Further, the cavity allows easy and direct entry of a stylet to the "working" element of the suction this tube 26, 27 or 28.

In one embodiment the manufacture of the sleeve is accomplished by employing DELRIN rod (an acetal thermoplastic resin) which is machined to the specification listed in foregoing.

The cavity 35 is obtained in two ways. (1) The sleeve and thin tubes are glued in place as stated above. A 0.167 inch to 0.169 inch drill bit is employed to drill through the joined sleeve and probe for 0.5 inch towards the sleeve's center. (2) The cavity is drilled into the joined end of the sleeve with no thin tube in place. From the proximal end of the sleeve a hole to accommodate the selected shaft is drilled penetrating into the cavity. The thin tube is glued in place after slightly penetrating the cavity 35. As stated in the above, both of these processes are envisioned to be replaced by injection molding techniques.

The lesser hardness of the sleeve guarantees the integrity of its stainless steel female counterpart the handle 9. Frictional degeneration is significantly lessened by the less hard sleeve on the handle.

Cavity 35 "The Flush Port" in the combined sleeve/probe is designed to accommodate standard syringes or provide easy entry for a stylet directly to the "working" element. As a direct result mid-procedural clogging or post operative processing is facilitated.

What is claimed in:

1. A medical/surgical wound suction device comprising:
   a first cylindrical elongated metal tube, having a first outer diameter and a first inner diameter;
   said first cylindrical elongated metal tube having a proximal open end and a distal open end;
   said distal open end being inwardly flared for a distance to a reduced diameter;
   a cylindrical plastic sleeve, said cylindrical sleeve having a proximal end portion and a distal end portion and a cylindrical intermediate portion therebetween;
   said intermediate portion having an outer diameter larger than the inner diameter of said first cylindrical elongated metal tube;
   said proximal end portion of said sleeve being tapered whereby it may be plugged at least partially into said flared distal open end of said first cylindrical elongated metal tube;
   said sleeve having a bore therethrough;
   a second cylindrical elongated metal tube;
   said second cylindrical metal tube having a proximal open end and a distal open end;
   said second cylindrical metal tube having said proximal open end fitted into said bore of said sleeve and extending from the sleeve at its distal end;
   said proximal open end of said second cylindrical metal tube terminating in said bore of said sleeve substantially midway said proximal end portion and said distal end portion;
   said proximal end portion of said sleeve having a cylindrical co-axle cavity contiguous with said bore of said sleeve said cavity having a bore of a larger diameter than the remainder of the bore of said sleeve;
   said cavity having a bottom contiguous with the proximal end of said cylindrical metal tube;
   whereby a luer of a hypodermic syringe carrying a cleansing fluid may be fitted into said cavity when said sleeve carrying said second cylindrical elongated metal tube is unplugged from said first cylindrical elongated metal tube and the cleansing fluid may be projected into and through said second cylindrical elongated metal tube;
   said first cylindrical metal tube having a port to the interior thereof intermediate its proximal and its distal end.

2. The medical/surgical suction device of claim 1, wherein the port on said first cylindrical elongated metal tube has a flat port surrounding member upon which a finger of an operator may be placed to open or close the port.

3. The medical/surgical suction device of claim 2, wherein the first cylindrical elongated metal tube has a bend intermediate the proximal open end and the distal open end and said port is located between said proximal open end and said bend.

* * * * *